United States Patent [19]
McCrorey

[11] 4,376,115
[45] Mar. 8, 1983

[54] METHOD AND COMPOSITION FOR TREATING TEETH AND METHOD FOR PREPARING SAME

[76] Inventor: Howard S. McCrorey, P.O. Box 4, Hudson, Wyo. 82515

[21] Appl. No.: 305,730

[22] Filed: Sep. 25, 1981

Related U.S. Application Data

[63] Continuation of Ser. No. 175,600, Aug. 5, 1980, abandoned.

[51] Int. Cl.$^3$ ............................................. A61K 33/30
[52] U.S. Cl. ................................................... 424/145
[58] Field of Search ......................................... 424/145

Primary Examiner—Stanley J. Friedman
Attorney, Agent, or Firm—Eric P. Schellin

[57] ABSTRACT

A composition for treating teeth comprising from about 10% to 20% by weight of blood root, approximately 5% to 15% by weight of powdered galangal root, and about 70% to 80% by weight of liquified zinc chloride in a suitable carrier for oral use. The composition is prepared by thorough admixture of the components under controlled conditions and aged before use. The composition may be applied to the teeth by means of a carrier such as a toothpaste, toothpowder, lozenges or mouthwash.

10 Claims, No Drawings

METHOD AND COMPOSITION FOR TREATING TEETH AND METHOD FOR PREPARING SAME

This is a continuation of application Ser. No. 175,600 filed Aug. 5, 1980, now abandoned.

This application relates to a composition and method for treating teeth.

The composition of the present invention is in a form that may conveniently be used for oral application. In treating the teeth, the most convenient types of formulations include toothpaste, toothpowder, lozenges, or mouthwash, since these forms of treatment make it unnecessary for the patient to frequent a hospital or dentist's office for treatment.

According to the present invention, crystalline zinc chloride is mixed with sufficient water to form a liquid zinc chloride. Powdered blood root and powdered galangal root are each passed through a 50- or 100-mesh screen, and mixed together. This mixture is added slowly with stirring to the zinc chloride solution to form a homogeneous paste. The paste is then aged, either at room temperature for one week, or in an oven at 55° C. to 65° C. for 4 to 8 hours.

Alternatively, crystalline zinc chloride is deliquesced or liquified in the presence of humid air at about room temperature to produce liquid zinc chloride. After the liquid zinc chloride is formed, it is thoroughly mixed with the powdered blood root, which contains the dried rhizomes of sanguinaria, and the powdered galangal root, sometimes known as India root or China root, which contains the dried rhizoma of *Alpinia officinarum*. The galangal root is a rhizome, indigenous to the Orient, and has an aggreeable aromatic odor. It contains a volatile oil and cinchol, an alcohol from cinchona resembling cholesterol. It is useful as an aromatic stimulant and resembles ginger in its qualities and effects. In view of the latter similarity to ginger, it is useful as a counterirritant. After thorough mixing, the composition is allowed to age in the presence of humid air at a temperature of 74° F., with additional intermittent mixing to permit thorough dispersing of the components and dissolution of the soluble components. During the mixing and aging, exposure to direct sunlight or metals is avoided, and after preparation it is packaged in glass containers which afford protection from sunlight.

It has been found that efficacious compositions are obtained when the composition contains from about 70% to 80% by weight of liquified zinc chloride, from about 10% to 20% by weight of powdered blood root, and from about 5% to 15% by weight of powdered galangal root.

The presence of the galangal root not only enhances the therapeutic effect of the compositions by enabling more rapid treatment of the teeth, but also improves the medicinal value of the preparation, so that stubborn conditions may be successfully treated. It has been found that, in the absence of galangal root, the mixture of zinc chloride and blood root has a caustic effect on gum tissue and thus is unsuitable for oral use. However, due to the presence of galangal root in the compositions of the present invention the caustic effect is avoided and there is little or no irritation or pain to the patient.

It is believed that the active ingredient in the present composition is formed by a reaction of components from the blood root and from the galangal root, this reaction being catalyzed by the zinc chloride solution. The active ingredient can be extracted from the mixture by fractionation with methanol, glacial acetic acid, acetone, chloroform, or other highly polar solvents.

The composition of the present invention is compatible with materials commonly present in oral preparations, for example, surface active agents, fluorine-providing compounds, and, when the oral preparations such as a dentifrice contain a sparingly soluble polishing material, that portion of the polishing material which is water-soluble or saliva-soluble.

The zinc chloride/blood root/galangal root, mixture may be employed generally in amounts ranging from about 0.01% to 10%, and preferably from 0.05% to 5%, by weight of the oral preparation.

In certain forms of the invention the oral preparation may be substantially liquid in character, such as a mouthwash or rinse. In such a preparation the vehicle is typically a water-alcohol mixture. Generally, the ratio of water to alcohol is in the range of about 1:1 to about 20:1, and preferably about 17:3, by weight. The total amount of water-alcohol mixture in this type of preparation is typically in the range of from 70% to 99.95% by weight of the preparation. The pH of such liquids is generally in the range of from 4.5 to 9, and typically from 5.5 to 8.

Because a high degree of foaming of the carrier is desirable in order to bring the active ingredient in contact with all the tooth surfaces, the liquid oral preparations of the present invention may also contain a foaming surface active agent. Anionic detergents such as sodium lauryl sulfate are particularly suitable for this purpose. The foaming agent is generally present in amounts ranging from about 0.05% to about 5% by weight of the composition.

In certain other forms of this invention, the oral preparation may be substantially solid or pasty in character, such as a toothpowder, or a toothpaste or dental cream. The dental vehicle of such solid or pasty oral preparations contains polishing material. Examples of polishing materials are water-insoluble sodium metaphosphate, potassium metaphosphate, tricalcium phosphate, dehydrated dicalcium phosphate, anhydrous dicalcium phosphate, calcium pyrophosphate, magnesium orthophosphate, trimagnesium phosphate, calcium carbonate, alumina, aluminum silicate, zirconium silicates, silica, plastics such as polymethyl methacrylate, bentonite, and mixtures thereof. Preferred polishing materials are crystalline silica, insoluble sodium metaphosphate, anhydrous dicalcium phosphate, and calcium carbonate, all of which typically are finely divided to have an average particle size below 10 microns.

Many of the so-called "water-insoluble" polishing materials are anionic in character and also include small amounts of soluble material. Thus, insoluble sodium metaphosphate may be formed in any suitable manner. The forms of insoluble sodium metaphosphate known as Madrell's salt and Kurrol's salt are further examples of suitable materials. These metaphosphate salts exhibit a minute solubility in water, and therefore are commonly referred to as insoluble metaphosphates. There is present therein a minor amount of soluble phosphate material as impurities, usually a few percent such as up to 4% by weight. The amount of soluble phosphate material, which is believed to be a soluble sodium trimetaphosphate in the case of insoluble sodium metaphosphate, may be reduced by washing with water if desired. The insoluble alkali metal metaphosphate is typically employed in powder form of a particle size such that no more than 1% of the material is larger than 37 microns.

The polishing material is generally present in amount in the range of from 20% to 99% by weight of the oral preparation. Preferably, it is present in amount in the range of from 20% to 75% in toothpaste and in the range of from 70% to 99% in toothpowder.

In pasty oral preparations, the zinc chloride/blood root/galangal root mixture is compatible with the polishing material and other components of the preparation. Thus, in a toothpaste, the liquid vehicle may comprise water, typically in a range of from 10% to 90% by weight of the preparation.

It is also desirable to use some humectant material in a toothpaste to keep it from hardening. Suitable humectants include glycerine, sorbitol, and other edible polyhydric alcohols. The humectant can comprise up to about 36% by weight of the toothpaste composition.

The solid or pasty oral preparation may also contain a surface active agent in order to achieve thorough and complete dispersion of the preparation throughout the oral cavity. The preferred organic surface active material is reasonably stable and forms suds throughout a wide pH range. Non-soap anionic synthetic detergents are particularly suitable. Examples of such materials are water-soluble salts of alkyl sulfate having from 10 to 18 carbon atoms in the alkyl radical, such as sodium lauryl sulfate; water-soluble salts of sulfonated monoglycerides of fatty acids having from 10 to 18 carbon atoms, such as sodium monoglyceride sulfonates; salts of $C_{10}$–$C_{18}$ fatty acid amides of taurine, such as sodium N-methyl-N-palmitoyl tauride; salts of $C_{10-C18}$ fatty acid esters of isothionic acid; and substantially saturated aliphatic acyl amides of saturated monoamino carboxylic acids having 2 to 6 carbon atoms and wherein the acyl radical contains 12 to 16 carbon atoms, such as sodium N-lauroyl sarcoside. Mixtures of two or more surface active agents can be used. It is preferred to use from 0.05% to 5% by weight of surface active material in the oral preparations of the present invention.

In certain forms of this invention a fluorine-providing compound may be present in the oral preparation. These compounds may be slightly soluble in water or may be fully water-soluble. They are characterized by the ability to release fluoride ions in water and by substantial freedom from reaction with other compounds of the oral preparation. Among these materials are inorganic fluoride salts, such as suitable alkali metal, alkaline earth metal, and heavy metal salts. Alkali metal and tin fluorides, such as sodium and stannous fluorides and mixtures thereof, are preferred.

The amount of the fluorine-providing compound is dependent to some extent upon the type of compounds, its solubility, and the type of oral preparation, but it must be a nontoxic amount. In a solid oral preparation, such as a toothpaste or toothpowder, it is considered that an amount of such compound which releases a maximum of 1% by weight, based on the weight of the preparation, of fluoride ion is satisfactory. Any suitable minimum amount of such compound may be used, but it is preferable to employ sufficient compound to release from 0.005% to 1%, most preferably about 0.1%, by weight of fluoride ion. Typically, in the cases of alkali metal fluoride and stannous fluoride, this component is present in an amount up to 2% by weight, based on the weight of the preparation, and preferably in the range of from 0.05% to 1%.

In a liquid oral preparation such as a mouthwash, the fluorine-providing compound is typically present in amount sufficient to release up to 0.13% by weight of fluoride ion.

Various other materials may be incorporated in the oral preparations of this invention. Examples are coloring or whitening agents, preservatives, silicones, chlorophyll compounds, and ammoniated material such as urea, diammoniumphosphate, and mixtures thereof. These adjuvants, where present, are incorporated in the preparations in amounts which do not substantially adversely affect the properties and characteristics desired.

Any suitable flavoring or sweetening materials may also be employed. Examples of suitable flavoring constituents are flavoring oils, e.g., oils of spearmint, peppermint, wintergreen, sassafras, clove, sage, eucalyptus, marjoram, cinnamon, lemon, orange, and methyl salicylate. Suitable sweetening agents include sucrose, lactose, maltose, sorbitol, and saccharin. Suitably, flavor and sweetening agent may together comprise from 0.01% to 5% or more of the preparation.

DESCRIPTION OF THE PREFERRED EMBODIMENTS

EXAMPLE I

The active tooth treating compound of the present invention may be prepared as follows:

|  | Grams |
| --- | --- |
| Zinc chloride | 3717.9 |
| Blood root, 50 mesh | 734.9 |
| Galangal root, 50 mesh | 489.9 |
| Deionized water | 1860.5 |

The zinc chloride was dissolved in water and the solution filtered through a coarse sintered glass filter. The sieved blood root and sieved galangal root are mixed together and added slowly with stirring to the zinc chloride solution to form a homogeneous paste. The paste is aged at room temperature for one week.

EXAMPLE II

The active tooth treating compound of the present invention may alternatively be prepared as follows:

|  | Grams |
| --- | --- |
| Zinc chloride | 3717.9 |
| Blood root, 100 mesh | 734.9 |
| Galangal root, 100 mesh | 489.9 |
| Deionized water | 1860.5 |

A homogeneous paste was formed from the above ingredients according to the procedure of Example I. The paste was transferred to Pyrex dishes and aged in an oven at 60° C. for 6 hours.

EXAMPLE III

The active tooth treating compound of the present invention may alternatively be prepared as follows:

|  | Parts by Weight |
| --- | --- |
| Powdered blood root | 586 |
| Powdered galangal root | 366 |

| -continued | |
|---|---|
| | Parts by Weight |
| Liquid size chloride | 3126 |

Crystals of zinc chloride are exposed to humid air for such period of time as is necessary to form a liquid zinc chloride material. The length of time required depends on the humidity of the air, the temperature thereof, and the dispersement of the crystals for exposure to the humid air.

To 3126 parts by weight of the liquid zinc chloride are added 586 parts by weight of the powdered blood root and 366 parts by weight of the powdered galangal root and the composition is thoroughly mixed. The composition may be periodically stirred over a period of perhaps ten days, not only to ensure thorough mixing, but also to facilitate solution of the soluble components of the blood root and the galangal root into the salve. It is normal for the composition to darken in color during this period of mixing and aging. At all times, the composition should be protected from sunlight and from contact with metals. Obviously, the precise proportions of the ingredients may vary from the specific proportions given above, and also the steps of preparation may be varied without departing from the present invention providing the mixing of the components is thorough and time is allowed to permit aging.

The composition of Example I was applied in a thin film to cavity sites which had been prepared as for filling. Temporary filling material was then applied to the treated cavity sites. Samples of tooth structure were removed at two week intervals by excavators and were observed by scanning electron microscopy. Clinically, the extracted material appeared dry, powdery, and harder than non-treated dentin. Pieces of excavated cavity tooth structure were irregularly shaped and showed no evidence of patent tubulas or microorganisms on any surface. No organisms were found on any surface.

Electron microscopic evaluation of dentin responses to the above composition showed an increase in tubula selerosis and hypermineralization of peritubular dentin. In order to ascertain whether elements of the dental pulp were involved, treated teeth were extracted at different time periods and prepared for viewing of the pulpal elements with electron microscopy. Tissues were fixed in paraformaldehyde and were decalcified in EDTA prior to being embedded in Epon. Thin sections were stained with lead citrate and uranyl acetate and viewed with electron microscopy.

Intact odontoblasts were found in all specimens lining the pulp below the site of the cavity restoration treated with the above composition. The odontoblasts demonstrated intachnuclei, abundant mitochondria, pigment granules, a Golgi complex, and many lipid droplets. Processes contained microfilaments and microtubulas. Most odontoblasts were flattened rather than cuboidal or columnar in shape. Some rough surfaced endoplasmic reticulum was seen, but most cells did not appear to be actively engaged in secreting matrix products at the time evaluated. No evidence of matrix selerosis or soft tissue cell calcification was evident in the dentin below the experimental cavity next to the pulp. Normal collagan distribution and matrix organization was evident. No evidence of odontoblast disintegration or elimical trauma was present. From this, it can be concluded that the pulp elements were not materially affected by treatment of tooth structure with the composition of Example I.

Additional studies of dentin treated with the composition of Example I confirm that selerosis of tubules is enhanced following treatment. Although microorganisms were found to be present in the tubules of the treated teeth, some of the microorganisms are mineralized and others show cloudy outlines and loss of internal ultrastructure, a condition indicative of lysis, and dissolution of the microorganisms. Tubule sclerosis is a normal response to carious invasion. Teeth treated with the above composition appear to have more sclerosis that forms in earlier stages and extends deeper into the tubules. This could be viewed as advantageous in reducing the possibility of pulpal exposure.

Additional teeth were prepared and treated with the composition of Example I. At select intervals ranging from one week to one month, samples of cavity preparation were excavated under aseptic conditions and inoculated into nutrient broth under both aerobic and anaerobic conditions. The broth was incubated at 37° C. for 48 hours, and the tubes were evaluated for bacterial growth. No bacterial growth was obtained from deep specimens, indicating that the viability of bacteria in treated teeth is absent. Although secondary invasion might occur from sites of leakage of poor restorations, it can be concluded that treated teeth do not have viable organisms in the tubules and that the composition of Example I can be considered a cariostatic agent.

EXAMPLE IV

A toothpaste of the following composition is prepared as by conventional methods:

| | Parts by Weight |
|---|---|
| Water | 39.08 |
| Sorbitol | 6.25 |
| Saccharin | 0.12 |
| Calcium pyrophosphate | 39.00 |
| Glycerine | 18.00 |
| Sodium alkyl (coconut) sulfate | 0.40 |
| Sodium coconut monoglyceride sulfonate | 0.75 |
| Sodium carboxymethyl cellulose | 1.15 |
| Composition of Example I | 0.50 |

EXAMPLE V

A mouthwash is prepared from the following ingredients:

| | Percent by Weight |
|---|---|
| Ethanol with flavoring | 16.430 |
| Anionic surfactant | 2.000 |
| Glycerine | 10.000 |
| Composition of Example I | 0.836 |
| Water | 70.814 |
| Sodium saccharin | 0.020 |

EXAMPLE VI

A toothpaste of the following composition is prepared by conventional methods.

| | Percent by Weight |
|---|---|
| Glycerine | 25.000 |
| Composition of Example I | 5.000 |
| Saccharin | 0.250 |

| -continued | |
|---|---|
| | Percent by Weight |
| Benzoic acid | 0.500 |
| Tragacanth | 1.850 |
| Polysorbate 80* | 2.000 |
| Mint flavor | 0.500 |
| Lustre-Phos H** | 43.000 |
| Deionized water | q.s. |

*Polyoxyethylene (20) sorbitan mono-oleate
**Calcium phosphate polishing agent, Monsanto Co.

What is claimed is:

1. A method for preparing a composition for treating teeth to reduce bacterial growth thereon comprising the steps of:
   a. exposing crystalline zinc chloride to air to liquify the same,
   b. mixing together about 10% to 20% by weight of powdered blood root and about 5% and 15% by weight of powdered galangal root to about 70% to 80% by weight of liquified zinc chloride; and
   c. intermittently and thoroughly mixing together the liquified zinc chloride and the mixture of powdered blood root and powdered galangal root over a period of time sufficient to permit aging of the mixture including solution of soluble components.

2. The method of claim 1 wherein the mixing and aging are carried out in the absence of direct sunlight and in metal free receptacles.

3. The method of claim 1 wherein the mixing and aging are carried out in the presence of humid air at a temperature of about 74° F.

4. A method for preparing a composition for treating teeth to reduce bacterial growth thereon comprising the steps of:
   a. mixing crystalline zinc chloride with sufficient water to form liquified zinc chloride;
   b. mixing together about 10% to 20% by weight of powdered blood root and about 5% to about 15% by weight of powdered galangal root to about 70% to 80% by weight of liquified zinc chloride and
   c. intermittently and thoroughly mixing together the liquified zinc chloride and the mixture of powdered blood root and powdered galangal root over a period of time sufficient to permit aging of the mixture including solution of soluble components.

5. The method of claim 4 wherein aging is conducted at a temperature from about 55° C. to about 65° C.

6. A composition for treating teeth to reduce bacterial growth thereon consisting essentially of a composition prepared by the following process:
   a. exposing crystalline zinc chloride to air to produce liquified zinc chloride;
   b. mixing together about 10% to 20% by weight of powdered blood root and about 5% to 15% by weight of powdered galangal root to about 70% to 80% by weight of liquified zinc chloride; and
   c. thoroughly mixing together the liquified zinc chloride and the mixture of powdered blood root and powdered galangal root over a period of time sufficient to permit aging of the mixture.

7. An oral preparation comprising the composition of claim 6 and vehicle compatible therewith.

8. The composition of claim 6 consisting essentially of about 75% by weight of liquified zinc chloride, about 15% by weight of powdered blood root, and about 10% by weight of powdered galangal root.

9. The composition of claim 6 consisting essentially of 3126 parts by weight of liquified zinc chloride, 586 parts by weight of powdered blood root, and 366 parts by weight of powdered galangal root.

10. A method for treating teeth to reduce bacterial growth thereon comprising applying to the teeth an effective amount of the composition of claim 6.

* * * * *